(12) United States Patent
Tai et al.

(10) Patent No.: US 10,501,766 B2
(45) Date of Patent: Dec. 10, 2019

(54) SYSTEM FOR OPTIMIZING FED-BATCH HYDROLYSIS OF BIOMASS

(71) Applicant: NUtech Ventures, Lincoln, NE (US)

(72) Inventors: Chao Tai, Decatur, IL (US); Deepak Keshwani, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 333 days.

(21) Appl. No.: 15/099,060

(22) Filed: Apr. 14, 2016

(65) Prior Publication Data

US 2016/0306916 A1 Oct. 20, 2016

Related U.S. Application Data

(60) Provisional application No. 62/147,642, filed on Apr. 15, 2015.

(51) Int. Cl.
*C12P 19/14* (2006.01)
*C12Q 3/00* (2006.01)
*C12P 19/02* (2006.01)
*C12M 1/00* (2006.01)

(52) U.S. Cl.
CPC ............ *C12P 19/14* (2013.01); *C12M 45/06* (2013.01); *C12P 19/02* (2013.01); *C12Q 3/00* (2013.01)

(58) Field of Classification Search
CPC .......... C12P 19/14; C12P 19/02; C12M 45/06
See application file for complete search history.

(56) References Cited

U.S. PATENT DOCUMENTS

2008/0064022 A1* 3/2008 Murthy ................. C12M 41/48
435/3

OTHER PUBLICATIONS

Chapwanya et al., "From Enzyme Kinetics to Epidemiological Models with Michaelis-Menton Contact Rate: Design of Nonstandard Finite Differences Schemes," 2012, 64:201-213 (Year: 2012).*
Haran, "An introduction to models for disease dynamics," 2009, obtained using Wayback Machine from Jul. 11, 2012 (Year: 2012).*
Adney and Baker "Measurement of cellulase activities." Laboratory analytical procedure 6, 1996.
Chandra et al., "The Influence of Pretreatment and Enzyme Loading on the Effectiveness of Batch and Fed-Batch Hydrolysis of Corn Stover," Biotechnol. Prog., 2011, 27:77-85.
Kermack and McKendrick, "A Contribution to the Mathematical Theory of Epidemics," Proc. R. Soc. London, Ser A, 1927,115:700-21.
Kim et al., "Pretreatment of corn stover by aqueous ammonia," Bioresour. Technol., 2003, 90:39-47.
Kristensen et al., "Yield-determining factors in high-solids enzymatic hydrolysis of lignocellulose," Biotechnol. Biofuels, 2009, 2:11.
Sluiter et al., "Determination of structural carbohydrates and lignin in biomass." Laboratory analytical procedure 1617, 2008.
Tai et al., "Epidemic based modeling of enzymatic hydrolysis of lignocellulosic biomass," Biotechnol. Prog., 2014, 30: 1021-1028.
Zaman et al., "Stability analysis and optimal vaccination of an SIR epidemic model," Biosystems, 2008, 93:240-249.

* cited by examiner

*Primary Examiner* — Matthew D Krcha
(74) *Attorney, Agent, or Firm* — Fish & Richardson P.C.

(57) ABSTRACT

Provided herein is a system for optimizing the fed-batch hydrolysis of biomass.

10 Claims, 8 Drawing Sheets

SYSTEM FOR OPTIMIZING FED-BATCH HYDROLYSIS OF BIOMASS

CROSS REFERENCE TO RELATED APPLICATIONS

This application claims the benefit of priority under 35 U.S.C. § 119(e) to U.S. Application No. 62/147,642 filed Apr. 15, 2015.

FEDERALLY SPONSORED RESEARCH OR DEVELOPMENT

This invention was made with government support under 2014-31100-06031 and 2015-31100-06031 awarded by the U.S. Department of Agriculture, National Institute of Food and Agriculture. The government has certain rights in the invention.

TECHNICAL FIELD

This disclosure generally relates to optimizing fed-batch hydrolysis of biomass.

BACKGROUND

Sugar production from lignocellulosic biomass is a key contributor to overall costs in the biomass-to-ethanol process, and enzymatic hydrolysis of cellulose offers advantages over other chemical conversion routes such as a mild operation environment, higher yields and minimal byproducts generation. Batch enzymatic hydrolysis with high solids loadings has been challenged by obstacles such as the elevation of reaction viscosity and inhibition by lignin, either through nonproductive binding or physical interference. Fed-batch approach has been studied and a potential advantage is the maintenance of a lower solids loading during the course of the hydrolysis reaction. Fed-batch operations enable superior control as they provide different avenues for process control through distinct phases of substrate digestion and enzyme consumption. By programming substrate feeding, one can control important phenomena such as solids content and end-product inhibition. Hence, the performance of fed-batch hydrolysis highly depends on timing and amount of substrate feeding operations.

The system described herein provides a method to optimize these control opportunities and still meet the desired objectives.

SUMMARY

This disclosure provides a system for optimizing the fed-batch hydrolysis of biomass.

In one aspect, a system is provided. Typically, such a system includes a process optimizer, which includes a processor and a computer-readable memory and a fed-batch hydrolysis controller. Generally, the processor and computer-readable memory is configured to: receive one or more target properties; determine, based on the one or more target properties, the one or more parameters by solving a viral epidemic-based SIR simulation using the one or more target properties as inputs to the viral epidemic-based SIR simulation; and transmit, to a fed-batch hydrolysis controller, the one or more parameters. Generally, the fed-batch hydrolysis controller is configured to: receive, from a process optimizer, one or more parameters; and cause a fed-batch hydrolysis to be performed according to the one or more parameter.

In some embodiments, causing the fed-batch hydrolysis to be performed according to the one or more parameters results in a fed-batch hydrolysis product having actual properties similar to the target properties.

In some embodiments, to solve a viral epidemic-based SIR simulation using the one or more target properties as inputs to the viral epidemic-based SIR simulation, the process optimizer is configured to use a measure of total biomass (enzyme-digestible biomass) as a Susceptibles input.

In some embodiments, to solve a viral epidemic-based SIR simulation using the one or more target properties as inputs to the viral epidemic-based SIR simulation, the process optimizer is configured to use a measure of enzyme-bound biomass (enzyme-bound-digestible biomass) as an Infectives input.

In some embodiments, to solve a viral epidemic-based SIR simulation using the one or more target properties as inputs to the viral epidemic-based SIR simulation, the process optimizer is configured to use a measure of biomass-digested sugars as a Removed input.

In some embodiments, to solve a viral epidemic-based SIR simulation using the one or more target properties as inputs to the viral epidemic-based SIR simulation, the process optimizer is configured to use the sum of a measure of total biomass, a measure of enzyme-bound biomass and a measure of biomass-digested sugars as a population size (N) input.

In some embodiments, to solve a viral epidemic-based SIR simulation using the one or more target properties as inputs to the viral epidemic-based SIR simulation, the process optimizer is configured to use a measure of total enzyme as a transmission constant input.

In some embodiments, to solve a viral epidemic-based SIR simulation using the one or more target properties as inputs to the viral epidemic-based SIR simulation, the process optimizer is configured to use a measure of biomass-digested sugars as a rate of removal input.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Part A

FIG. 3 are graphs showing modified SIR model behavior with different transmission and removing rates in sensitivity analysis for enzymatic hydrolysis with 5% substrate (w/v)

and 10 FPU/g cellulose of enzyme (kinetic parameters and fitting errors are listed in Table 3).

Part B

DETAILED DESCRIPTION

A mathematical control strategy for optimizing a feeding operation was developed for fed-batch enzymatic hydrolysis of dilute acid pretreated lignocellulosic biomass. Using the model described herein, cellulose conversion was maximized and glucose concentration achieved the highest possible value over a fixed hydrolysis time. Boundaries of feeding rate and lignin content were set for feasible controls. Effects of solids loadings in feeding source on hydrolysis performance were also studied. Using the optimal control feeding strategy, glucose concentration and accumulated cellulose conversion reached up to 77.31 g/L and 72.08% in 100 hr, respectively, which are 108.76% and 37.50% higher than in a batch hydrolysis with the same amount of enzyme consumption but not optimized using the model described herein. Optimal control is a useful tool for guiding operations in fed-batch and continuous processes as it enables process optimization through clear objective functions and feasible controls.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part A

Example 1—The Model

A different perspective of enzyme behaviors in adsorption and catalysis has been investigated and a compartmental model used in epidemiology was modified to simulate the enzymatic hydrolysis of dilute acid pretreated lignocellulosic biomass based on similarity in behaviors of disease spread and enzyme attack in certain environments.

Original SIR Model

In the formulation of this model, population N is divided into three categories:

S: the Susceptible class, those who may catch the disease but currently are not infected;

I: the Infected class, those who are infected with the disease and are contagious; and R: the Removed class, those who have recovered from the disease permanently, are naturally immune, or have died.

See, Allman and Rhodes, 2004, *Mathematical Models in Biology: An Introduction*, New York: Cambridge University Press. In the three compartmentalized settings, members of population progress through the three classes, where Susceptibles are either disease-free or becoming infected; Infectives are passing disease to Susceptibles through contact until they are removed permanently from the disease; and the Removed individual will never be infected again. Based on this mechanism, if population N is fixed, the model scheme can be described as follows (Eqs. 1-4):

$$\frac{d_S}{d_t} = -\beta SI \quad (1)$$

$$\frac{d_I}{d_t} = \beta SI - rI \quad (2)$$

$$\frac{d_R}{d_t} = rI \quad (3)$$

$$N = S + I + R \quad (4)$$

where $\beta$ is a transmission constant, which is determined by the fraction of contacts made by Infectives and Susceptibles, and the probability of certain contact is effective; r is the Removal rate, which is dependent on how fast Infectives can recover from disease.

Modified SIR Model for Enzymatic Hydrolysis

The enzyme behavior in hydrolysis of cellulose can be simulated as virus spreading in a certain population, where enzyme attacks and adsorbs onto Susceptibles in the substrate, forming enzyme-substrate (ES) complex which corresponds to Infectives, then the complex is catalyzed into glucose, which corresponds to the Removed class and would never be infected again.

Figure 1:
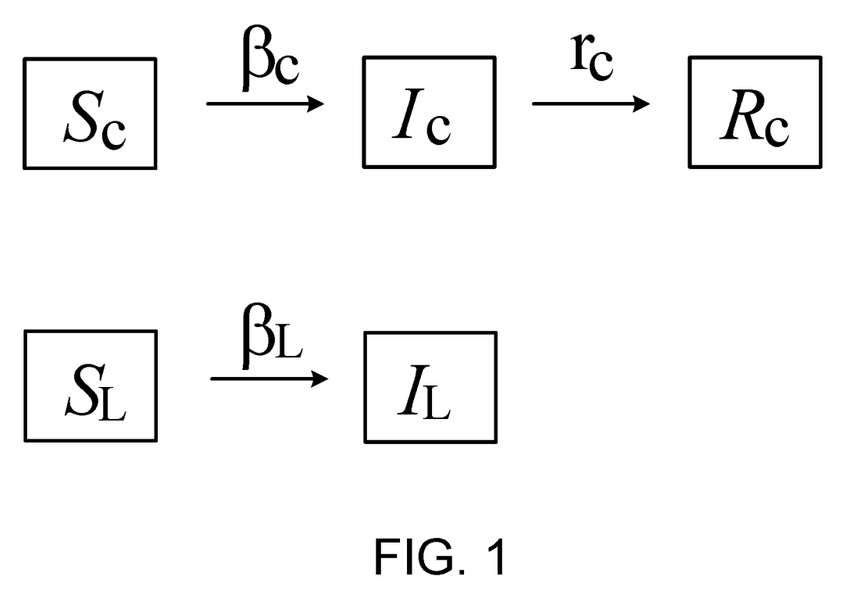
FIG. 1 is a schematic showing the modified SIR model for enzymatic hydrolysis of dilute acid pretreated lignocellulosic biomass.

The main components in dilute sulfuric acid pretreated biomass are cellulose and lignin (hemicellulose removal is the primary mode of action for dilute acid pretreatment), and enzyme can be adsorbed to both of them (Boussaid and Saddler, 1999, Enzyme Microb. Technol., 24:138-43). The process of enzyme being adsorbed by lignin is generally considered as irreversible (Kim et al., 2003, Bioresour. Technol., 90:39-47), so infected lignin cannot pass enzyme to other components and, hence, lignin can only be infected by free enzyme or enzyme de-adsorbed from infected cellulose. In addition, the enzyme cannot digest lignin, so there's no removed class for lignin. Based on these facts, the original SIR model has been modified to the scheme described in FIG. 1 and as below (Eqs. 5-10):

$$\frac{d_{S_c}}{d_t} = -\beta_c S_c I_c \quad (5)$$

$$\frac{d_{I_c}}{d_t} = \beta_c S_c I_c - r_c I_c \quad (6)$$

$$\frac{d_{R_c}}{d_t} = r_c I_c \quad (7)$$

$$\frac{d_{S_L}}{d_t} = -\beta_L S_L I_c \quad (8)$$

$$\frac{d_{I_L}}{d_t} = \beta_L S_L I_c \quad (9)$$

$$N = S_c + S_L + I_c + I_L + R_c \quad (10)$$

Where Susceptibles and Infectives have been divided into two classes for cellulose and lignin, respectively. But only cellulose Infectives are contagious and can pass enzyme to both Susceptibles. Lignin Susceptibles, once infected, will stay as carriers (Infectives but not infectious, such as Dengue fever) permanently. From the Eqs. 5 to 9, we can see that the transmission rates of $\beta_c$ and $\beta_L$ are independent; $\beta_L$ does not have any effect on the formation of removed cellulose ($R_c$), so the model can be simplified to be more focused on the infective and removing process of cellulose. Furthermore, transmission of enzyme to lignin can be considered as an inhibition role of lignin to the transmission of enzyme to cellulose, because both contacts made by cellulose Infectives to Susceptibles and probability of effective contacts are decreasing with the presence of lignin in the substrate. To include this inhibition role, the transmission constant $\beta_c$ is modified to $$\frac{S_c}{S_L}$$

$\beta_c$ to dynamically represent the severity of the effect based on the quantity ratio of Susceptibles of cellulose and lignin as cellulose being digested. At the same time, enzyme activity cannot be assumed to remain the same during the whole adsorption and catalysis process because of glucose inhibition, thermal and mechanical inactivation, and some other not fully-known reasons. Based on these complex causes, enzyme activity can be considered as decreasing over the hydrolysis time period, which, in the model, can be represented by $$\frac{r_c}{t}$$

instead of a constant $r_c$ alone. With these two considerations, the modified SIR model for enzymatic hydrolysis of dilute acid pretreated lignocellulosic biomass is shown below (Eqs. 11-14):

$$\frac{d_{S_c}}{d_t} = -\frac{S_c}{S_L} \beta_c S_c I_c \quad (11)$$

$$\frac{d_{I_c}}{d_t} = \frac{S_c}{S_L} \beta_c S_c I_c - \frac{r_c}{t} I_c \quad (12)$$

$$\frac{d_{R_c}}{d_t} = \frac{r_c}{t} I_c \quad (13)$$

$$N = S_c + I_c + R_c \quad (14)$$

Example 2—Materials

Corn stover was collected from Rogers Memorial Farm (Lincoln, Nebr.) in 2012. The corn stover was air dried, milled, screened through 2.36 mm sieve and homogenized in a single lot. The enzyme preparation used in this work was Cellic CTec2, which was kindly provided by Novozymes North America Inc.

Example 3—Pretreatment Experiment

Corn stover samples were pretreated with 1.75% (w/v) sulfuric acid in sealed flasks in an autoclave at 135° C. for 160 min. Solid to liquid ratio was 1:10. The pretreated biomass recovered by filtration through a porcelain Buchner funnel was washed with distilled water until the pH was 7. The wet solids were completely transferred to a pre-weighed plastic bag, weighed and stored sealed at 4° C. for the enzymatic hydrolysis later. A small portion of the wet pre-treated biomass was weighed and dried for composition analysis.

Example 4—Enzymatic Hydrolysis

Batch enzymatic hydrolysis experiments were conducted in 50 mL total volume in 125 mL screw-top Erlenmeyer flasks with substrate loadings varied from 5% to 15% (w/v). For each substrate loading, three enzyme loading dosages were applied, ranging from 5 to 60 FPU/g cellulose. The activity of CTec2 was determined by standard procedure developed by National Renewable Energy Laboratory (NREL); 0.05 mol/L sodium citrate buffer was used to maintain a pH 5.0 and tetracycline (0.004%, w/v) and cycloheximide (0.003%, w/v) were added to the hydrolysis mixture to prevent microbial growth. The hydrolysis was carried out at 50° C. and 150 rpm for 72 hr in a controlled environmental incubator shaker (Model I26, New Brunswick Scientific, NJ). Aliquots of 0.3 mL were taken at specified time intervals during hydrolysis and centrifuged at 10,000 rpm for 10 min; the supernatant were used for sugar analysis.

TABLE 1

Initial Values Inputted into MATLAB to Run the Optimization Function

| Hydrolysis Conditions | | Initial Values | | | |
|---|---|---|---|---|---|
| Substrate Loading (W/V, %) | Enzyme Loading (FPU/g Cellulose) | Sc (g/L) | SL (g/L) | Ic (g/L) | Rc (g/L) |
| 5 | 5 | 28.00 | 16.65 | 0.1 | 0 |
| 5 | 60 | 28.00 | 16.65 | 0.1 | 0 |
| 10 | 5 | 56.10 | 33.31 | 0.1 | 0 |
| 10 | 60 | 56.10 | 33.31 | 0.1 | 0 |
| 15 | 5 | 84.20 | 49.97 | 0.1 | 0 |
| 15 | 60 | 84.20 | 49.97 | 0.1 | 0 |

Example 5—Composition and Sugar Analysis

Chemical composition of raw and pretreated corn stover were analyzed using standard analytical procedures developed by NREL Sugars in the hydrolysate were measured in a HPLC system (Model Ultimate 3000, Dionex, IL) with a Bio-Rad Aminex HPX-87P column (300 mm×7.8 mm), a Bio-Rad De-Ashing guard column, and a refractive index detector. The mobile phase was HPLC grade water at a flow rate of 0.6 mL/min and the column temperature was 85° C.

Example 6—Estimation of Kinetic Parameters

The model was formed as a set of differential equations in MATLAB (R2013a, the MathWorks, MA). The symbolic solutions were obtained using ODE45 solver. The optimization function, lsqcurvefit was used to fit the model solutions to experimental data to estimate kinetic parameters. The initial values inputted into MATLAB to run the optimization function are provided in Table 1.

Example 7—Model Validation and Sensitivity Analysis

Model validation in enzymatic hydrolysis was performed by the calculation of RMSE (root mean square error) and $R^2$ described as below (Eqs. 15 and 16) based on the residuals and resnorm given by the function of lsqcurvefit:

$$RMSE = \sqrt{\frac{\sum_1^n ((fun(t) - R_c)^2)}{n}} \quad (15)$$

$$R^2 = 1 - \frac{\sum_1^n ((fun(t) - R_c)^2)}{\sum_1^n \left(\left(R_c - \frac{1}{n}\sum_1^n R_c\right)^2\right)} \quad (16)$$

where fun(t) is the model predicted data at each hydrolysis time point while $R_c$ is experimental data, and n is the number of samples for model fitting.

The sensitivity analysis of the adsorption negative role of lignin and enzyme activity inhibition over time was analyzed by the comparison of experimental data and model predicted data with and without the corresponding parameters and items. Enzyme activity inhibition over time was also compared to inhibition caused only by glucose.

Example 8—Model Analysis

One of the major concerns about the simulation of enzyme adsorption as virus spread is the difference in transmission behavior.

TABLE 2

Estimated Kinetic Parameters and Fitting Errors in Modified SIR Model

Hydrolysis Conditions

| Substrate Loading (W/V, %) | Enzyme Loading (FPU/g Cellulose) | $\beta_c$ | $r_c$ | RMSE | $R^2$ |
|---|---|---|---|---|---|
| 5 | 5 | 0.2143 | 0.0782 | 0.1414 | 0.9965 |
| 5 | 60 | 0.2766 | 0.4857 | 1.6542 | 0.9468 |
| 10 | 5 | 0.1108 | 0.0910 | 0.3830 | 0.9949 |
| 10 | 60 | 0.2209 | 0.3844 | 2.0114 | 0.9758 |
| 15 | 5 | 0.0176 | 0.0721 | 0.8838 | 0.9738 |
| 15 | 60 | 0.0793 | 0.2727 | 2.2141 | 0.9825 |

A virus can be transmitted from single Infective individual to multiple Susceptibles while the Infective can still stay as infected with virus, however, Infectives (ES complex) in enzymatic hydrolysis cannot behave in this way. Most of the time, once effectively adsorbed to substrate, enzyme can only de-adsorb from the complex after the catalysis reaction is done, which means Infectives in this case cannot pass virus/enzyme to Susceptibles until the moment they are Recovered. To differentiate this fact from the original SIR model, while still maintaining the same model formation, the transmission constant in the enzymatic hydrolysis case can be interpreted in a different way. The transmission constant in the original SIR model is determined by the multiplication of two factors, the fraction of contacts made by Infectives and Susceptibles, and the probability of effective contacts. While the contacts made by Infectives and Susceptibles cannot be changed because of the existing structures of cellulose and lignin, the probability of effective contacts can be considered as extremely low during the infection stage before Infectives become recovered.

TABLE 3

Estimated Kinetic Parameters and Fitting Errors in Sensitivity Analysis for Enzymatic Hydrolysis with 5% Substrate (w/v) and 10 FPU/g Cellulose of Enzyme

Figure 3:
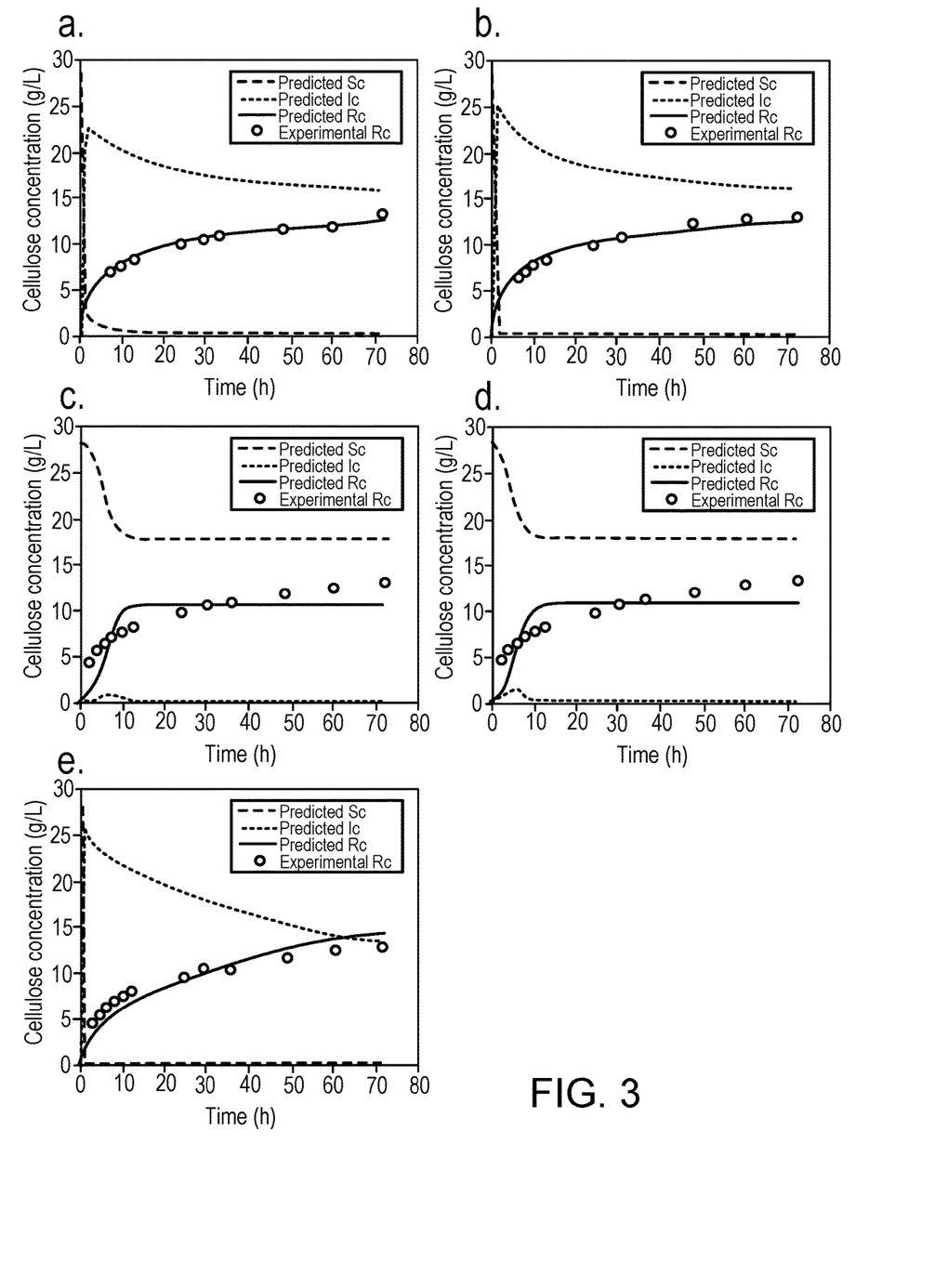

| Caption in FIG. 3 | Transmission Constant | Removing Constant | $\beta_c$ | $r_c$ | RSME | R2 |
|---|---|---|---|---|---|---|
| a | $\frac{S_c}{S_{L_{\beta_c}}}$ | $\frac{r_c}{t}$ | 0.2312 | 0.1288 | 0.4240 | 0.9857 |
| b | $\beta_c$ | $\frac{r_c}{t}$ | 0.3073 | 0.1251 | 0.4491 | 0.9840 |
| c | $\beta_c$ | $r_c$ | 0.1029 | 2.3269 | 1.8545 | 0.7272 |
| d | $\frac{S_c}{S_{L_{\beta_c}}}$ | $r_c$ | 0.0464 | 1.3886 | 1.9215 | 0.7071 |
| e | $\frac{S_c}{S_{L_{\beta_c}}}$ | $\frac{r_c}{R_c}$ | 51.7545 | 0.0834 | 1.0306 | 0.9158 |

Example 9—Kinetic Parameters in the Modified SIR Model

Compared to the previous kinetic models, which were based on the combination of Langmuir adsorption and Michaelis-Menten catalysis mechanism, the kinetic parameters in the present model are relatively much simpler because the former approach requires about 15 parameters to make the complex model formation work. Although this large number of parameters can describe the adsorption and catalysis processes in detail, it is hard to analyze the model behavior prediction and rate-determining step because the exact values of these parameters are mutually influenced when obtained from MATLAB. In addition, more experiments such as determining enzyme adsorption to solids have to be conducted to obtain certain parameters, while enzyme protein distribution data is not needed at all to obtain parameters values in this modified SIR model. Two kinetic parameters in the present model can fully describe the enzymatic hydrolysis process with one being responsible for adsorption, and the other being responsible for catalysis, and with only experimental recovered cellulose data. The model can predict enzyme distribution information, which includes quantities of enzyme protein being adsorbed to cellulose, lignin and free in the liquid.

Figure 2:
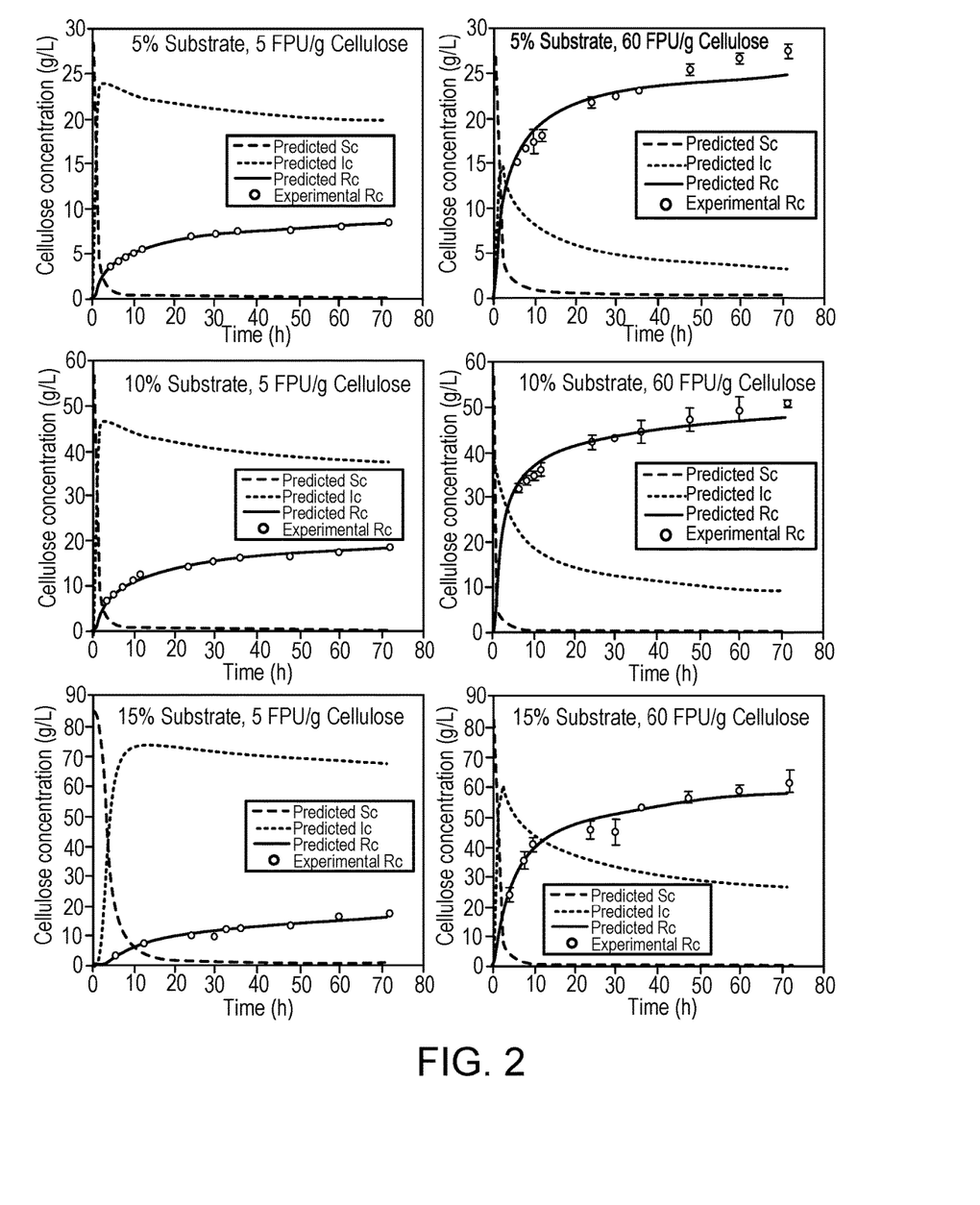
FIG. 2 are graphs showing modified SIR model behavior and experimental data on enzymatic hydrolysis of dilute acid pretreated corn stover with different substrate and enzyme loadings.

The experimental data of enzymatic hydrolysis with 5% to 15% substrate loadings (w/v) was used to obtain kinetic parameters by data fitting and optimization in MATLAB. For every substrate loading, 5 and 60 FPU/g cellulose of enzyme were loaded to cover the typical loading ranges (Table 2). The behaviors of model compartments and experimental cellulose conversion data are shown in FIG. 1. The constants of $\beta_c$ and $r_c$ in Table 2 have to be multiplied by $$\frac{S_c}{S_L}$$

and $$\frac{1}{t},$$

respectively, to become the transmission and removal constants at corresponding time points of hydrolysis. For each substrate loading, both $\beta_c$ and $r_c$ increase with the elevation of enzyme loading. While for the same enzyme loading, $\beta_c$ decreases sharply with the elevation of substrate loading, indicating strong inhibition effects of high substrate content on enzyme adsorption to cellulose. At the same time, the catalysis rates at 5 FPU/g cellulose in three substrate loadings are almost stable but significantly lower than at 60 FPU/g cellulose, indicating the rate-determining step for lower enzyme loading is the catalysis step. This can also be seen in FIG. 2 where most of the Susceptibles become Infectives in the initial stage of hydrolysis, but the infectives cannot recover due to the low catalysis rate. On the other hand, although the catalysis rates at 60 FPU/g cellulose are much higher, the elevation of substrate loadings make them decrease, and the sharp removing process of Infectives gets shorter (FIG. 2), which leads directly to the slowing down of glucose production in the middle stage of hydrolysis.

There is a threshold in this SIR model based on which we can evaluate whether the infection will continue at certain time point. In the original SIR model (Eqs. 1 to 4), if the infection is happening, then DI has to be greater than 0, as shown in Eq. 17:

$$\Delta I=(\beta S-r)I>0 \quad (17)$$

So when $$S > \frac{r}{\beta}$$

at a specific time point, then the infection will continue, while, when $$S = \frac{r}{\beta},$$

then there will be no more Infectives and the process will stop.

In the modified SIR model (Eqs. 11-14), $\Delta I$ is presented in Eq. 18 with the consideration of lignin block effect and enzyme activity inhibition over time:

$$\Delta I = \left(\frac{S_c}{S_L}\beta_c S_c - \frac{r_c}{t}\right)I_c > 0 \quad (18)$$

With the arrangement of variables and parameters, the threshold becomes: when $$\frac{S_c^2}{S_L} > \frac{r_c}{\beta_c t}$$

at a specific time point, the infection will continue. After the time point when $$\frac{S_c^2}{S_L} = \frac{r_c}{\beta_c t},$$

the block effect of lignin will be dominant and enzyme de-adsorbed from partially digested cellulose cannot be adsorbed again by cellulose such that no new Infectives will be formed, the catalysis process will continue until the existing Infectives are removed.

Example 10—Model Validation

In previous Michaelis-Menten based models, most of the kinetic parameters are fixed based on the corresponding adsorption and reaction mechanisms, and the models are validated by the changing values of variables such as substrate or glucose concentrations. SIR-based models cannot be validated in the same way, because every time the population (initial substrate) or virus quantity (enzyme loading) is changed in certain environments, the transmission constant for infection and removal rate will be changed because the contact frequency and probability of effective contacts are changing. So in the present case, the modified SIR model was validated by the calculation of RMSE and $R^2$, which are shown in Table 2. The model fit cellulose conversion data, and predicted the infection of the substrate with enzyme and the removal process (i.e. product formation) with satisfactory accuracy, with $R^2$ ranging from 0.9468 to 0.9965 and small RMSE values. The decline in $R^2$ for 60 FPU/g cellulose loadings can be clearly seen in the later stage of hydrolysis (FIG. 2) where the experimentally-removed cellulose concentrations are higher than the model predicted values, indicating that the inhibition effect on the rate of catalysis in the later stage is not as strong as in the model.

Example 11—Sensitivity Analysis of Transmission and Removal Rates

To evaluate the performance of modified transmission and removal constants in the model, the sensitivity analysis of block effect of lignin and inhibition effect over time was performed with different transmission and removal constants, respectively, in hydrolysis with 5% substrate and 10 FPU/g cellulose of enzyme. The model behaviors with different constants are shown in FIG. 3 and kinetic parameters and fitting errors are shown in Table 3. As we can see, the best fit came with $$\frac{S_c}{S_L}\beta_c \text{ and } \frac{r_c}{t},$$

while keeping the transmission constant as $\beta_c$ alone can predict the removed cellulose well with $R^2$ up to 0.9840. But we can see in FIG. 3b that, without considering the block effect of lignin, all the cellulose in substrate has been infected to ES complex in the first 2 h.

Compared to the change of transmission constant, keeping removal rate as $r_c$ would lead the model to reach a plateau phase where, after around 12 hr, no more Susceptibles can become Infectives because $$S_c = \frac{r_c}{\beta_c}$$

in FIG. 3c and $$\frac{S_c^2}{S_L} = \frac{r_c}{\beta_c}$$

in FIG. 3d. With the change of removal constant to $$\frac{r_c}{R_c},$$

which assumes the catalysis rate of enzyme was only inhibited by removed cellulose (glucose), the model behavior was predicted in FIG. 3e. The Susceptibles all got infected by enzyme in a very short time, but the removal rate was lower than experimental values in the early stage of hydrolysis, indicating the inhibition on enzyme activity in the model was stronger than observed. However, the model over-predicted recovered cellulose in the later stage, implying that the removal process will extend at a relatively high rate if the batch hydrolysis continues after 72 h, which indicates that the inhibition on enzyme activity in the model was smaller than observed. These sensitivity analyses showed the block effect of lignin on enzyme adsorption has to be considered. Keeping removal constant $r_c$ alone without considering inhibition effect would lead the model to plateau in a short time, while including only glucose inhibition cannot fully correct model behavior.

Example 12—Original SIR Model Notation

Original SIR model:
I=infective class
N=population
R=removed class
S=susceptible class
β=transmission constant
r=removal constant
In modified SIR model:
$I_c$=cellulose infective concentration at a given time (g/L)
$I_L$=lignin infective concentration at a given time (g/L)
$R_c$=removed cellulose concentration at a given time (g/L)
$S_c$=cellulose susceptible concentration at a given time (g/L)
$S_L$=lignin susceptible concentration at a given time (g/L)
t=hydrolysis time (h)
$\beta_c$=transmission constant to cellulose)
$\beta_L$=transmission constant to lignin
$r_c$=removal constant of cellulose infective Part B Example 13—Materials Corn stover was collected from Rogers Memorial Farm (Lincoln, Nebr.) in 2012. The corn stover was air dried, milled, screened through 2.36 mm sieve and homogenized in a single lot. The enzyme preparation used in this work was Cellic CTec2, which was provided by Novozymes North America Inc. (Franklinton, N.C.).

Example 14—Pre-Treatment

Corn stover samples were pretreated with 1.75% (w/v) sulfuric acid in sealed flasks in an autoclave at 135° C. for 160 min. Solid to liquid ratio was 1:10. The pretreated biomass recovered by filtration through a porcelain Buchner funnel was washed with distilled water until the pH was 7. The wet solids were completely transferred to a pre-weighed plastic bag, weighed and stored sealed at 4° C. for the enzymatic hydrolysis later. A small portion of the wet pretreated biomass was weighed and dried for composition analysis.

Example 15—Enzymatic Hydrolysis

Batch enzymatic hydrolysis experiments were conducted in 50 mL total volume in 125 mL screw-top Erlenmeyer flasks with substrate loadings varied from 5 to 15% (w/v) and enzyme loadings from 5 to 60 FPU/g cellulose. The activity of CTec2 enzyme was determined by a standard procedure developed by National Renewable Energy Laboratory (NREL) (Adney and Baker, 1996). 0.05 mol/L sodium citrate buffer was used to maintain a pH of 5.0, and tetracycline (0.004%, w/v) and cycloheximide (0.003%, w/v) were added to the hydrolysis mixture to prevent microbial growth. The hydrolysis was carried out at 50° C. and 150 rpm for 72 hr in a controlled environmental incubator shaker (Model I26, New Brunswick Scientific, NJ). Aliquots of 0.3 mL were taken at specified time intervals during hydrolysis and centrifuged at 10,000 rpm for 10 min, and the supernatant was used for sugar analysis.

Fed-batch hydrolysis was conducted in a 1.3 L bioreactor (Model BioFlo115, New Brunswick Scientific, NJ) with 300 mL initial loading volume, which contains 10% (w/v) pretreated biomass and 20 FPU/g cellulose of enzyme. The remaining hydrolysis conditions were the same as in batch hydrolysis. The pretreated biomass feeding operation was guided by the calculated optimal control strategy presented in this study and was controlled by a programmed doser (Lambda Lab Instruments, Brno, Czech Republic). The moisture content of feeding substrate in the doser was 2.38%. The enzyme feeding was at a consistent rate corresponding to biomass feeding to maintain the enzyme loading in the reactor at 20 FPU/g cellulose.

Chemical composition of pretreated corn stover was analyzed using standard analytical procedures developed by NREL (Sluiter et al., 2008, National Renewable Energy Laboratory (NREL), Report #42621, Golden, Colo.; Sluiter et al., 2011, National Renewable Energy Laboratory (NREL), Report #42618, Golden, Colo.). Sugars in the hydrolysate were measured in a HPLC system (Model Ultimate 3000, Dionex) with a Bio-Rad Aminex HPX87P column (300 mm×7.8 mm) and a refractive index detector. The mobile phase was HPLC grade water at a flow rate of 0.6 mL/min and the column temperature was 85° C.

Example 16—Modeling Theory and Optimal Control Strategy

Figure 4:
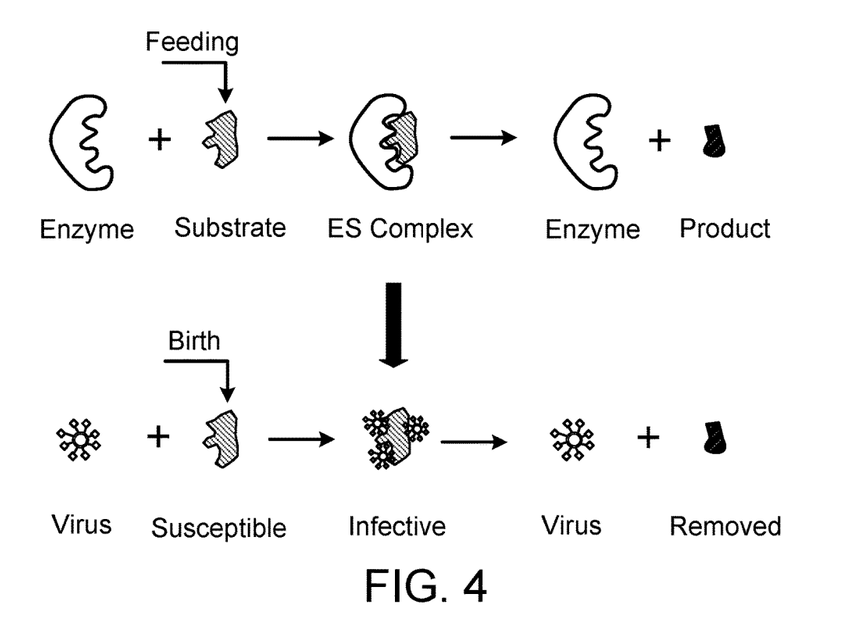
FIG. 4 is a schematic showing the fed-batch modified SIR model for enzymatic hydrolysis of dilute acid pretreated lignocellulosic biomass.

An epidemic based model was previously developed to describe the enzymatic hydrolysis of dilute acid pretreated corn stover (Tai et al., 2014, Biotechnol. Prog., 30:1021-8). The process of substrate getting adsorbed and digested by enzyme was simulated as susceptibles getting infected by viruses and becoming removed and recovered. With the consideration of changes brought by feeding operations, such as the negative effect of accumulated lignin and system volume change, the batch hydrolysis model was modified and extended to describe fed-batch hydrolysis as described in FIG. 4 and Eq. 1-5:

$$\frac{dS_c}{dt} = -\frac{S_c}{S_L}\beta_c S_c I_c + \frac{uDA}{V} - S_c\frac{u}{10^3 V} \quad (1)$$

$$\frac{dI_c}{dt} = \frac{S_c}{S_L}\beta_c S_c I_c - \frac{r_c}{t}I_c - I_c\frac{u}{10^3 V} \quad (2)$$

$$\frac{dR_c}{dt} = \frac{r_c}{t}I_c - R_c\frac{u}{10^3 V} \quad (3)$$

$$S_L = (S_c + I_c + R_c)\frac{B}{A} \quad (4)$$

$$\frac{dV}{dt} = \frac{u}{10^3} \quad (5)$$

In the above equations, u is the feeding rate of wet pretreated substrate, which is equivalent to the birth rate in the original SIR model (Allman and Rhodes, 2004, *Mathematical Models in Biology; an Introduction*, New York: Cambridge University Press; Kermack and McKendrick, 1927, Proc. R. Soc. London, Ser A, 115:700-21). Once the newly fed biomass comes into the system, the cellulose part $$\frac{uDA}{V}$$

becomes $S_c$, which is the substrate in this model, and progresses to the Infectives (ES complex) and the Removed class, which is glucose. The lignin part is included in the item $S_L$ (Eq. 4) and the accumulated negative effect of lignin to enzyme adsorption is represented in item $$\frac{S_c}{S_L}\beta_c.$$

For the optimal control problem formulation, there are four state variables, $S_c$, $I_c$, $R_c$ and V, and the objective function (Eq. 6) is to maximize cellulose conversion during processing and glucose concentration at the end point of hydrolysis (T). The biomass feeding rate u is the control variable that needs to be optimized, and is bounded by Eq. 7.

$$\max \int_0^T \frac{R_c}{S_c + I_c + R_c} dt + R_{c(T)} \quad (6)$$

$$\min\left(\frac{7V}{DA}, \frac{(R_{c(i)} - R_{c(i-1)})V}{hDA}\right) \leq u \leq \max\left(\frac{7V}{DA}, \frac{(R_{c(i)} - R_{c(i-1)})V}{hDA}\right) \quad (7)$$

where 7 g/L/h is the maximum glucose productivity ever observed in our batch hydrolysis, i=1, 2, . . . , N is the count in vector $R_c$ and h is time step size. So the biomass feeding rate, u, is bounded to supply certain amount of cellulose in a range between the real digested cellulose and the possible maximum amount. Another bounded condition in this model is the solids content in the system. The objective function of maximizing cellulose conversion guarantees smooth hydrolysis process, so the limitation considered here is lignin content in the current system. When it is over 12%, the feeding rate of biomass will be set to 0 at that moment (Eq. 8).

$$\text{If } (S_c + I_c + R_c)\frac{B}{A} \times 10^{-3} > 12\%, \text{ then } u = 0; \quad (8)$$

The last bounded condition that was set in this formulation is that, when hydrolysis time reaches 24 h before the end set point T, the feeding operation stops to allow sufficient time for digestion.

The kinetic parameters were established based on batch hydrolysis performance (Table 4). The parameters for feeding substrate and initial conditions are listed in Table 4. Using the Hamiltonian equation and Pontryagin's maximum principle (Lenhart and Workman, 2007, London, UK: Chapman & Hall/CRC; Zaman et al., 2008, Biosystems, 93:240-9), the optimal trajectory was solved in MATLAB (R2013a, the MathWorks, MA).

TABLE 4

Values of Parameters for Modeling and Initial Conditions for State Variables

| Parameters | Values | State variables | Initial values |
| --- | --- | --- | --- |
| A | 52.99% | $S_c$ | 52.89 |
| B | 33.15% | $S_L$ | 33.15 |
| D | 97.62% | $I_c$ | 0.10 |
| T | 100 | $R_c$ | 0 |
| $\beta_c$ | 0.2204 | V | 0.3 |
| $r_c$ | 0.1622 | | |

Example 17—Model Analysis

Figure 5:
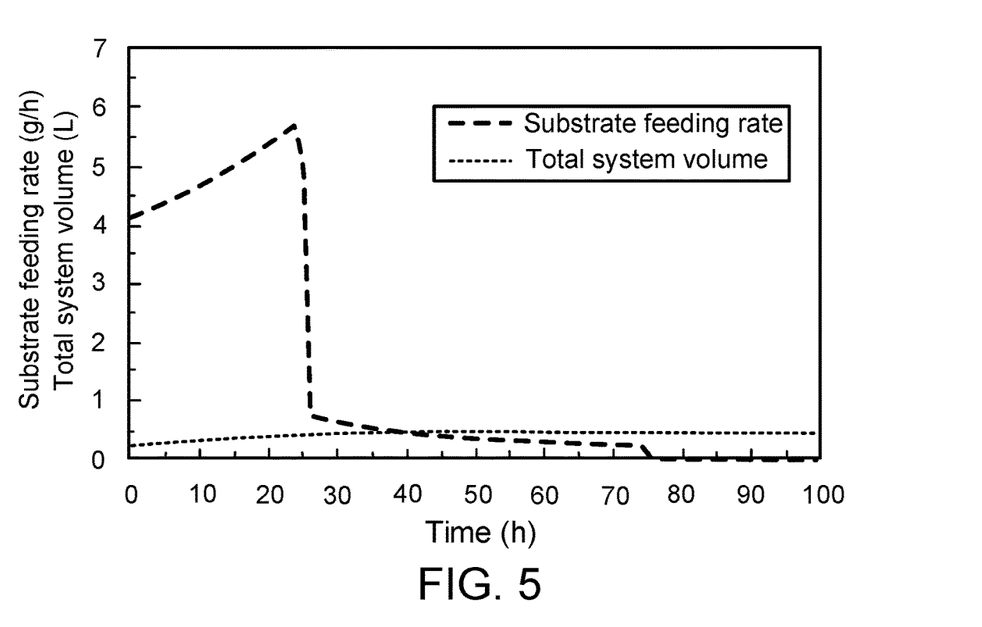
FIG. 5 is a graph showing the substrate feeding rate and total system volume change in optimal control strategy with objective function of maximizing cellulose conversion and glucose concentration at the end.
Figure 6:
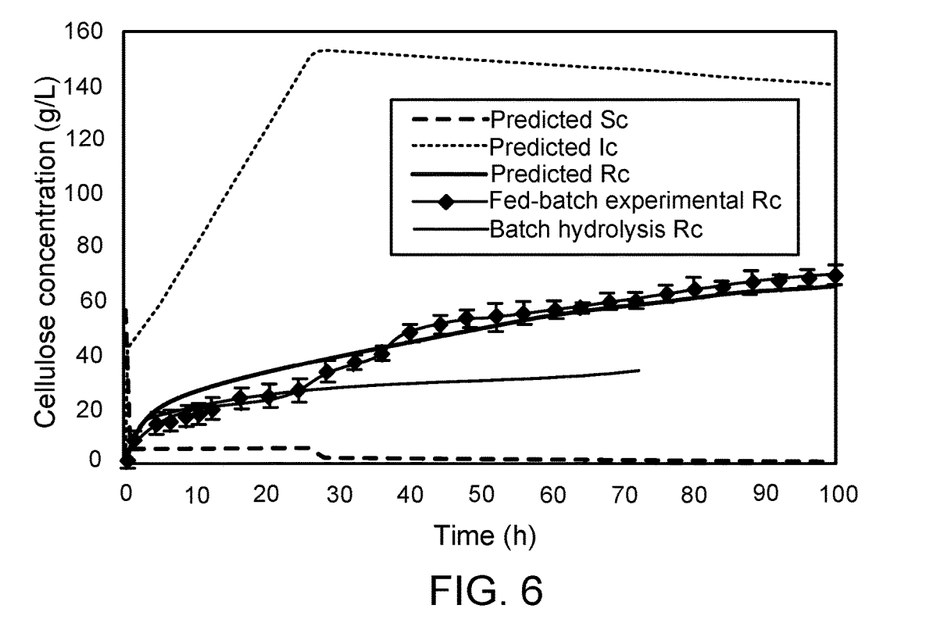
FIG. 6 is a graph showing a comparison of model prediction and experimental fed-batch hydrolysis result guided by optimal control feeding.

The optimal control problem was solved using an iterative method with Euler's procedure (Kamien and Schwartz, 2012, New York: Courier Dover Publications). The state variables were solved with initial values and then swept forward in time, while the adjoint system was solved backward in time. After every iteration of state and adjoint variables, u was calculated according to optimality condition. Since the control u was bounded in this problem, the value of Hamiltonian equation was evaluated for the selection of u. Before the value of u can be plugged into the calculation of the next iteration of the state and adjoint variables, lignin content in the system was checked to make sure it would not exceed 12% if u is greater than 0. The iteration would stop once the error criteria was met in the program setting; the optimal control strategy was solved in FIG. 5 and the model predicted result is shown in FIG. 6.

One of the most important problems in epidemiology is to ascertain whether a termination of disease occurs only when no Susceptibles are left, or the interplay of various factors in infection and recovery may result in termination while Susceptibles are still present in the unaffected population (Kermack and McKendrick, 1927, supra). There is a threshold in this modified fed-batch SIR model based on whether the infection will continue or not at one time point. With the existence of enzyme in the system, part of the cellulose Susceptibles would always progress into Infectives through enzyme adsorption unless it is completely blocked by lignin, so the progress-determine variable is $\Delta I_c$. If the infection is moving forward, then A/c has to be greater than 0, as shown in Eq. 9:

$$\Delta I_c = \left(\frac{S_c}{S_L}\beta_c S_c - \frac{r_c}{t} - \frac{u}{10^3 V}\right)I_c > 0 \quad (9)$$

With the arrangement of variables and parameters, the threshold becomes Eq. 10:

$$u < 10^3 V\left(\frac{S_c}{S_L}\beta_c S_c - \frac{r_c}{t}\right) \quad (10)$$

When this threshold is met at any time during the conversion, the infection will continue, which clearly indicates the feeding control u is bounded inside the model formation. If u is greater than the above threshold (Eq. 10), the block effect of lignin will be dominant and enzyme that is de-adsorbed from partially digested cellulose cannot be adsorbed again by cellulose, such that no new Infectives can be formed.

Example 18—Enzymatic Hydrolysis Performance

Fed-batch hydrolysis started with an initial loading of 10% substrate and 20 FPU of enzyme/g cellulose and was then guided by optimal control strategy. The feeding control u and total system volume change are shown in FIG. 5. The feeding control started at almost a linear rate, which increased sharply, indicating that the model predicts cellulose in the substrate is being digested well, and lignin content at this feeding rate is not severely interfering mass transfer in the system in the first 25 hr. Right after the fast feeding period, there is a sharp drop at around 25 hr, which was treated as a turning point in piecewise continuous function for feeding and applied to the programmed substrate doser. The turning point was followed by gradually decreasing feeding rate, which then turned to 0 at 76 h. This feeding strategy fits the objective functions described herein. The payoff item in the function is glucose concentration (digested cellulose concentration) at the end of hydrolysis. To maximize glucose concentration in a certain period of time, cellulose feedings need to be maximized in spite of bringing in lignin at the same time. With another objective of maximizing cellulose conversion during a certain period of time, cellulose has to be fed into system as early as possible to allow enough time for digestion. With the bounded control conditions for feeding rate and lignin content in the system, the maximized substrate feeding rate is limited in the range from 4.17 to 5.61 g/hr, which is equivalent to a range of from 2.16 to 2.90 g/hr for cellulose.

The comparison between this fed-batch hydrolysis guided by the optimal control operation and the model prediction is shown in FIG. 6. The experimentally-digested cellulose concentration matches well with the model predicted except for the first 32 hr. Compared to the batch hydrolysis with the same initial loadings, the interference with feedings in fed-batch was not significant on hydrolysis progression for the first 24 hr. However, the digested cellulose concentration was significantly lower than the model predicted results during the period of time from 6 to 32 hr. This fed-batch performance is interesting because the substrate is being fed at a maximized possible rate for the first 25 hr. With the solids being brought into the system, the hydrolysis rate (cellulose digestion rate) was expected to be lower than in batch hydrolysis where no interference is being made. The result here might be due to the fact that, although the hydrolysis rate for the feeding process was lower, the digestion of newly added cellulose would make the glucose concentration the same as in batch hydrolysis. This result agrees with a former fed-batch study where the manual feeding operations were conducted in a relatively high frequency in the first 4 and 12 hr (Chandra et al., 2011, Biotechnol. Prog., 27:77-85).

After 24 hr, the digested cellulose concentration is sharply increased, until about 40 hr. This makes sense because the feeding rate of the substrate dropped to 0.69 g/hr. With significantly less substrate coming into the system, the overall hydrolysis rate would go up very quickly with a consistent amount of enzyme. However, it would not last long because the enzyme de-adsorbed from partially digested cellulose would be adsorbed to lignin more and more, with the increasing ratio of accumulated lignin over residual cellulose. The glucose concentration and accumulated cellulose conversion reached up to 77.31 g/L and 72.08% at the end of hydrolysis, which are 108.76% and 37.50% higher than in batch hydrolysis with the same amount of enzyme consumption.

Example 19—Modeling with Different Solids Loadings

Figure 7:
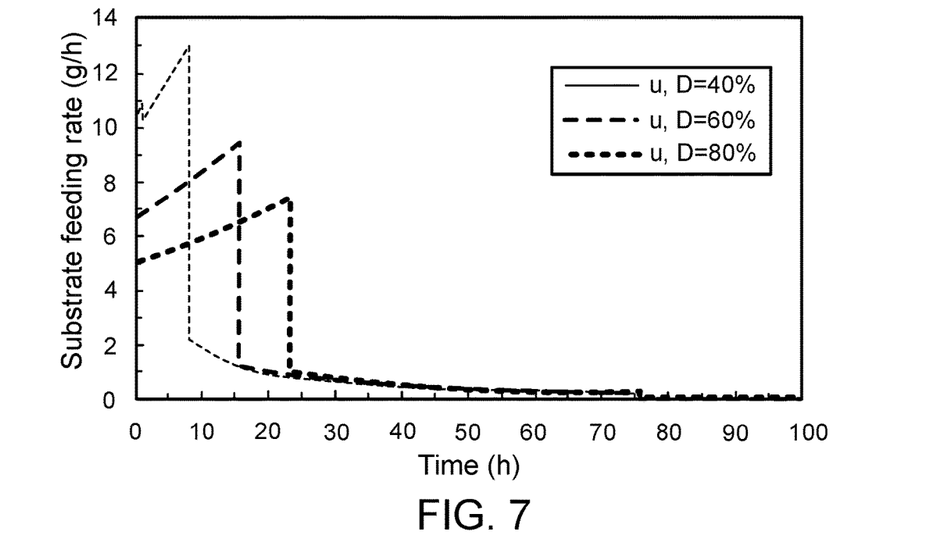
FIG. 7 is a graph showing the substrate feeding rates in optimal control strategy for three different solids loadings in feeding sources.
Figure 8:
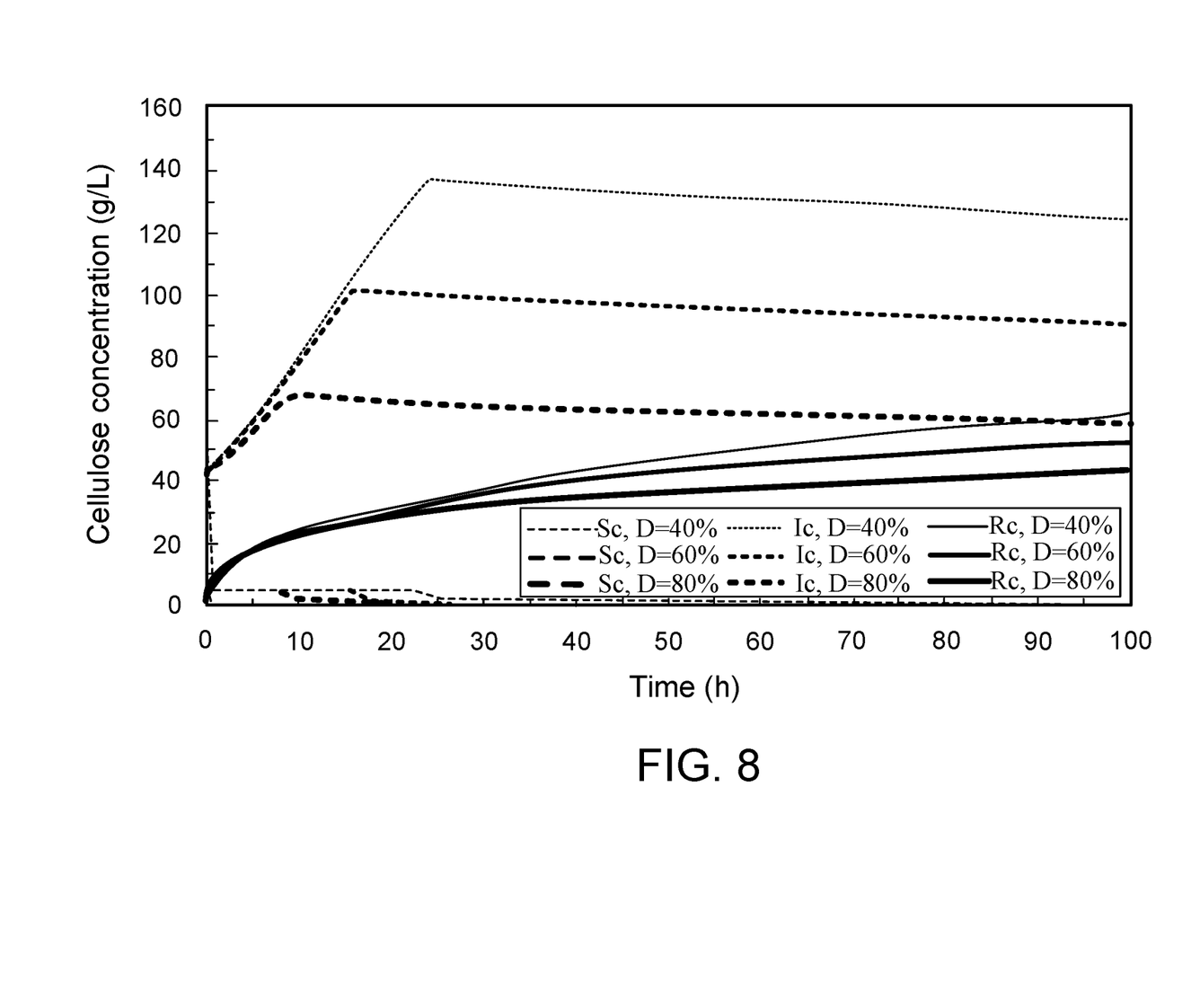
FIG. 8 is a graph showing a comparison of model predictions for fed-batch hydrolysis performances with three different solids loadings in feeding sources.

It has been well established that solids loading is one of the key factors in enzymatic hydrolysis of lignocellulosic biomass (Kristensen et al., 2009, Biotechnol. Biofuels, 2:11). Therefore, solids loading in the feeding source is expected to play a key role in fed-batch hydrolysis because of its direct influence on solids content in the current system, once the feedings come into the system. To compare the effects of different solids loadings on the hydrolysis performance, the optimal control strategy with the same objective function was solved with three different solids loadings in the feeding substrate, 40%, 60% and 80%. The optimized feeding rate control for each solids loading is shown in FIG. 7 and the model predicted result for hydrolysis performance is shown in FIG. 8. The feeding controls have similar trends as in FIG. 5. However, the slope for the linear increase in the initial stage for the 40% solids loading is significantly greater than the other two, and the value of feeding rate is almost the sum of the other two, indicating the interference on mass transfer brought by feeding substrate on the current hydrolysis system is significantly small because of the 60% water being brought into the system together with the pretreated biomass. With the balance of cellulose conversion and glucose concentration at the end as the objective function, the initial fast feeding of 40% solids stops early at 8 hr, with the consideration that the more water the feeding brings in, the harder it is for glucose concentration to reach a high value. The initial fast feeding rate for 80% solids is the lowest among the three, but it lasts the longest, indicating that it brings a bigger interference on the system. With only 20% water in the feeding source, the new feeding can only come into the system when the previous feeding was digested properly, otherwise, the accumulated solids could cause problems in mass transfer and possible enzyme transition to new substrate.

For each solids loading, there is a unique feeding strategy (FIG. 7) that results in distinct hydrolysis profiles, which are shown in FIG. 8. Most of the cellulose in the substrate has been infected by enzyme in the very initial stage of hydrolysis and the Susceptibles have been maintained in a low concentration with a consistent supply of enzyme. The Infectives concentration for 40% solids is the lowest among the three because of the significantly higher percentage of water being brought into system, while the highest Infectives concentration for 80% solids feeding reached up to 13.68%, indicating the solids content in the system is well controlled by the bounded condition of 12% lignin during optimization.

Optimal control strategy with the modified SIR model described herein successfully solved and guided feeding operations for fed-batch enzymatic hydrolysis of lignocellulosic biomass with a target of maximizing cellulose conversion and glucose concentration at the end of the process. Solids and lignin contents were controlled during the process and the model satisfactorily predicted the experimental result using optimized feeding control. Different objective functions can be formed with the consideration of different targets such as minimizing the usage of feeding source if the cost of raw material is high or solely maximizing the final product concentration if conversion percentage is not deemed to be critical. A different control variable or multiple control variables can be selected based on the understanding of the model and the feasibility for operation. Optimal control strategy can be widely applied in fed-batch or continuous processes with a clear objective and it provides the benefit of automatic process operation.

Example 20—Nomenclature in Modified Model

Figure 9:
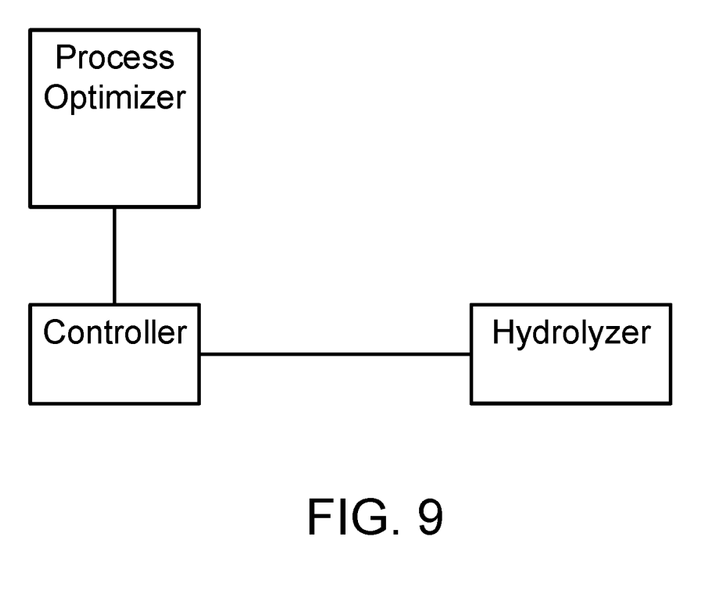
FIG. 9 is a block diagram of a hydrolyzer controlled by a controller receiving input from a process optimizer.

Cellulose content in dry pretreated biomass (constant, %)
Lignin content in dry pretreated biomass (constant, %)
D Dry solids content in wet pretreated biomass (constant, %)
h Time step size (h)
i Count in variable vector
$I_c$ Cellulose infective concentration at a given time (g/L)
$R_c$ Removed cellulose concentration at a given time (g/L)
$S_c$ Cellulose susceptible concentration at a given time (g/L)
$S_L$ Lignin susceptible concentration at a given time (g/L)
t Hydrolysis time (h)
T Hydrolysis end time (constant, h)
u Feeding rate of wet pretreated biomass (g/h)
V Current volume of reaction system (L)
$\beta_c$ Enzyme adsorption constant to cellulose (transmission constant to cellulose)
$r_c$ Removal constant of cellulose infective FIG. 9 is a block diagram of a hydrolyzer controlled by a controller receiving input from a process optimizer.

Figure 10:
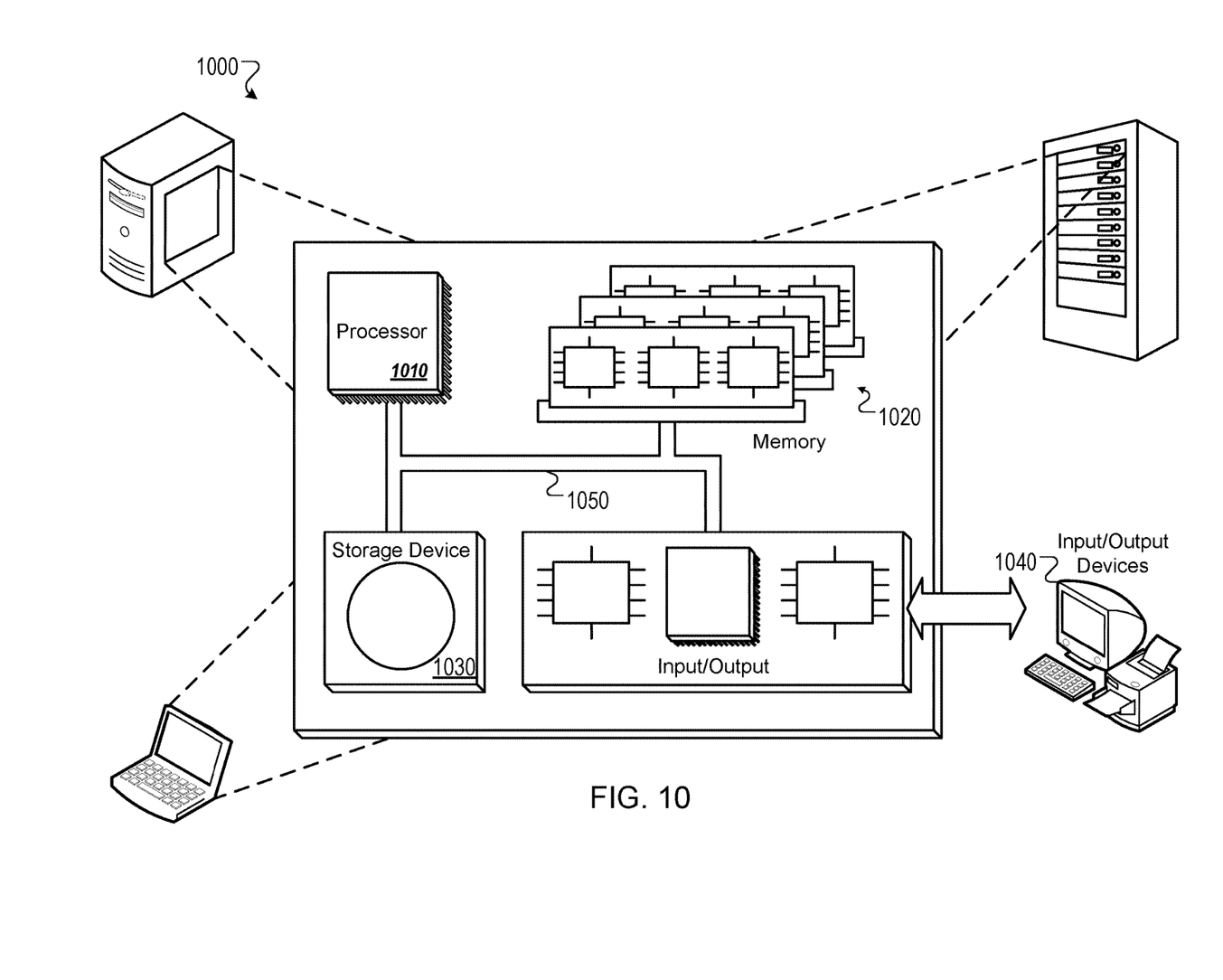
FIG. 10 is a is a schematic diagram that shows an example of a computing system.

FIG. 10 is a schematic diagram that shows an example of a computing system 1000. The computing system 1000 can be used for some or all of the operations described previously, according to some implementations. The computing system 1000 includes a processor 1010, a memory 1020, a storage device 1030, and an input/output device 1040. Each of the processor 1010, the memory 1020, the storage device 1030, and the input/output device 1040 are interconnected using a system bus 1050. The processor 1010 is capable of processing instructions for execution within the computing system 1000. In some implementations, the processor 1010 is a single-threaded processor. In some implementations, the processor 1010 is a multi-threaded processor. The processor 1010 is capable of processing instructions stored in the memory 1020 or on the storage device 1030 to display graphical information for a user interface on the input/output device 1040.

The memory 1020 stores information within the computing system 1000. In some implementations, the memory 1020 is a computer-readable medium. In some implementations, the memory 1020 is a volatile memory unit. In some implementations, the memory 1020 is a non-volatile memory unit.

The storage device 1030 is capable of providing mass storage for the computing system 1000. In some implementations, the storage device 1030 is a computer-readable medium. In various different implementations, the storage device 1030 may be a floppy disk device, a hard disk device, an optical disk device, or a tape device.

The input/output device 1040 provides input/output operations for the computing system 1000. In some implementations, the input/output device 1040 includes a keyboard and/or pointing device. In some implementations, the input/output device 1040 includes a display unit for displaying graphical user interfaces.

Some features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM (erasable programmable read-only memory), EEPROM (electrically erasable programmable read-only memory), and flash memory devices; magnetic disks such as internal hard disks and removable disks; magneto-optical disks; and CD-ROM (compact disc read-only memory) and DVD-ROM (digital versatile disc read-only memory) disks. The processor and the memory can be supplemented by, or incorporated in, ASICs (application-specific integrated circuits).

To provide for interaction with a user, some features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

Some features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN (local area network), a WAN (wide area network), and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

This document describes technologies that can be applied to a wide range of uses, which are designed and intended to be beneficial for all users involved. However, some of the technologies described may be put to illegitimate, malicious, and even illegal ends by bad actors. This is true with almost any technology, but there is often a greater sensitivity when a technology interacts with a user's security and private information. The described technologies all are designed to operate in an environment and in a manner that respects the rights of all users. As such, features such as user notification, opt-in and opt-out procedures and privacy settings are available options to be used to ensure user security and privacy are respected.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A system to hydrolyze biomass comprising:
    a hydrolyzer comprising a fed-batch hydrolysis controller and configured to:
        operate to hydrolyze a batch of biomass under the controller of the fed-batch hydrolysis controller, wherein the operation is managed by the hydrolyzer according to one or more hydrolyzer-inputs that each define a physical setup of a particular element of the hydrolyzer; a process optimizer comprising a processor and a computer-readable memory, the process optimizer configured to:
    receive one or more target properties;
    determine, based on the one or more target properties, one or more target parameters by solving a viral epidemic-based SIR simulation using the one or more target properties as inputs to the viral epidemic-based SIR simulation, wherein, to solve a viral epidemic-based SIR simulation using the one or more target properties as inputs to the viral epidemic-based SIR simulation, the process optimizer is configured to use a measure of total biomass as a Susceptibles input and wherein, to solve a viral epidemic-based SIR simulation using the one or more target properties as inputs to the viral epidemic-based SIR simulation, the process optimizer is configured to use a measure of enzyme-bound biomass as an Infectives input, and wherein, to solve a viral epidemic-based SIR simulation using the one or more target properties as inputs to the viral epidemic-based SIR simulation, the process optimizer is configured to use a measure of biomass-digested sugars as a Removed input; and
    transmit, to a fed-batch hydrolysis controller, the one or more target parameters; and wherein the fed-batch hydrolysis controller configured to:
    receive, from a process optimizer, the one or more target parameters;
    determine one or more hydrolyzer-settings based on the target parameters, each of the hydrolyzer-settings defining a parameter of operation of the hydrolyzer; and
    instructing the hydrolyzer to operate to hydrolyze a batch of biomass by using the hydrolyzer-settings for the hydrolyzer-inputs in the instructed operation;
    wherein one of the one or more target parameters is feeding rate.

2. The system of claim 1, wherein causing the fed-batch hydrolysis to be performed according to the one or more parameters results in a fed-batch hydrolysis product having actual properties similar to the target properties.

3. The system of claim 1, wherein, to solve a viral epidemic-based SIR simulation using the one or more target properties as inputs to the viral epidemic-based SIR simulation, the process optimizer is configured to use a sum of a measure of total biomass, a measure of enzyme-bound biomass and a measure of biomass-digested sugars as a population size input.

4. The system of claim 1, wherein, to solve a viral epidemic-based SIR simulation using the one or more target properties as inputs to the viral epidemic-based SIR simulation, the process optimizer is configured to use a measure of total enzyme as a transmission constant input.

5. The system of claim 1, wherein, to solve a viral epidemic-based SIR simulation using the one or more target properties as inputs to the viral epidemic-based SIR simulation, the process optimizer is configured to use a measure of biomass-digested sugars as a rate of removal input.

6. A method of hydrolyzing biomass comprising:
    receiving one or more target properties;
    determining, based on the one or more target properties, one or more target parameters by solving a viral epidemic-based SIR simulation using the one or more target properties as inputs to the viral epidemic-based SIR simulation, wherein solving a viral epidemic-based SIR simulation using the one or more target properties as inputs to the viral epidemic-based SIR simulation comprises using a measure of total biomass as a Susceptibles input and wherein solving a viral epidemic-based SIR simulation using the one or more target properties as inputs to the viral epidemic-based SIR simulation comprises using a measure of enzyme-bound biomass as an Infectives input, and wherein solving a viral epidemic-based SIR simulation using the one or more target properties as inputs to the viral epidemic-based SIR simulation comprises using a measure of biomass-digested sugars as a Removed input;

determining one or more hydrolyzer-settings based on the target parameters, each of the hydrolyzer-settings defining a parameter of operation of the hydrolyzer; and hydrolyzing a batch of biomass according to the one or more target parameter by using the hydrolyzer-settings for hydrolyzer-inputs that each define a physical characteristic of the hydrolyzing;

wherein one of the one or more target parameters is feeding rate.

7. The method of claim 6, wherein hydrolyzing a batch of biomass according to the one or more parameter results in a fed-batch hydrolysis product having actual properties similar to the target properties.

8. The method of claim 6, wherein solving a viral epidemic-based SIR simulation using the one or more target properties as inputs to the viral epidemic-based SIR simulation comprises using a sum of a measure of total biomass, a measure of enzyme-bound biomass and a measure of biomass-digested sugars as a population size input.

9. The method of claim 6, wherein solving a viral epidemic-based SIR simulation using the one or more target properties as inputs to the viral epidemic-based SIR simulation comprises using a measure of total enzyme as a transmission constant input.

10. The method of claim 6, wherein solving a viral epidemic-based SIR simulation using the one or more target properties as inputs to the viral epidemic-based SIR simulation comprises using a measure of biomass-digested sugars as a rate of removal input.

* * * * *